US008257334B2

(12) United States Patent
Buell et al.

(10) Patent No.: US 8,257,334 B2
(45) Date of Patent: Sep. 4, 2012

(54) DISPOSABLE PANT-TYPE DIAPER HAVING IMPROVED PROTECTION AGAINST RED MARKING

(75) Inventors: Kenneth Barclay Buell, Cincinnati, OH (US); Gregory Ashton, Kobe (JP); Craig Andrew Hawkins, Ashiya (JP); William Robert Vinnage, Jr., Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1021 days.

(21) Appl. No.: 10/366,176

(22) Filed: Feb. 13, 2003

(65) Prior Publication Data

US 2003/0120240 A1 Jun. 26, 2003

Related U.S. Application Data

(60) Division of application No. 09/700,559, filed on Nov. 16, 2000, now abandoned, which is a continuation of application No. PCT/US98/10841, filed on May 28, 1998.

(51) Int. Cl.
*A61F 13/15* (2006.01)
*A61F 13/20* (2006.01)

(52) U.S. Cl. ............................ 604/394; 604/396; 2/400

(58) Field of Classification Search ............ 604/385.01, 604/388–392, 385.29, 358, 393, 394, 396, 604/402, 386; 428/103; 2/400, 401, 403, 2/404, 406, 407

See application file for complete search history.

(56) References Cited

U.S. PATENT DOCUMENTS 4,920,617 A * 5/1990 Higashinaka .................. 24/442
5,163,932 A * 11/1992 Nomura et al. .......... 604/385.29
5,569,234 A * 10/1996 Buell et al. .................... 604/396
5,624,420 A * 4/1997 Bridges et al. ................ 604/396
5,626,574 A * 5/1997 Sasaki et al. ............. 604/385.29
5,931,827 A * 8/1999 Buell et al. ............... 604/385.29
6,537,644 B1 * 3/2003 Kauschke et al. ............ 428/103
2002/0032427 A1 * 3/2002 Schmitz et al. .......... 604/385.11

FOREIGN PATENT DOCUMENTS

EP 0 483 692 A1 5/1992
EP 0 657 153 A2 6/1995
EP 0983758 A1 * 3/2000
WO WO 96/31179 10/1996
WO WO 97/30671 8/1997
WO WO 98/18421 5/1998

* cited by examiner

*Primary Examiner* — Melanie Hand
(74) *Attorney, Agent, or Firm* — Charles R. Ware

(57) ABSTRACT

A disposable pull-on garment is provided having a front region, a back region and a crotch region. The garment includes a chassis having edge lines in the front and back regions. A pair of extensible front ear panels extends laterally outward from the chassis in the front region, and a pair of extensible back ear panels extends laterally outward from the chassis in the back region. Each of the panels is joined along its outermost edge line to its corresponding opposite front or back ear panel to form two overlapping seams, two leg openings and a waist opening. At least one of the overlapping seams has a substantially bonded portion and an unbonded portion such that the ratio in the length of the unbonded portion to the substantially bonded portion is between about 4:96 and about 20:80.

12 Claims, 10 Drawing Sheets

DISPOSABLE PANT-TYPE DIAPER HAVING IMPROVED PROTECTION AGAINST RED MARKING

CROSS-REFERENCE TO RELATED APPLICATION

This is a divisional of U.S. application Ser. No. 09/700,559 filed on Nov. 16, 2000 now abandoned, which is continuation of International Application PCT/US98/10841 filed on May 28, 1998.

FIELD

The present invention relates to disposable pull-on garments and methods for making the same. Examples of such disposable pull-on garments include disposable underwear, disposable pull-on diapers and training pants, and disposable panties for menstrual use. More specifically, the present invention relates to disposable pull-on garments which have improved protection against red marking while maintaining improved fitness to body.

BACKGROUND

Infants and other incontinent individuals wear disposable garments such as diapers to receive and contain urine and other body exudates. Disposable pull-on garments having fixed sides, which are also called "pant type" garments, have become popular for use on children able to walk and often who are toilet training. These pull-on garments have side panels with edges that are seamed together to form two leg openings and a waist opening. In order to contain body exudates as well as fit a wide variety of body shapes and sizes, these pull-on garments need to fit snugly about the waist and legs of the wearer without drooping, sagging or sliding down from its position on the torso. Examples of these pull-on garments are disclosed, for example, in U.S. Pat. No. 5,171,239 issued to Igaue et al. on Dec. 15, 1992; U.S. Pat. No. 4,610,681 issued to Strohbeen et al. on Sep. 9, 1986; U.S. Pat. No. 4,940,464 issued to Van Gompel et al. on Jul. 10, 1990; U.S. Pat. No. 5,246,433 to issued Hasse et al. on Sep. 21, 1993; U.S. Pat. No. 5,569,234 issued to Buell et al. on Oct. 29, 1996; and WO 96/31176 (Ashton) published on Oct. 10, 1996.

To prevent pull-on garments from drooping, sagging or sliding down from the torso of wearer, it is believed that a proper force should be generated at the waist and side panel areas of pull-on garments and applied to the torso of the wearer. For example, U.S. Pat. No. 5,415,649 issued to Watanabe et al. on May 16, 1995, discloses the use of elastic members which have different expanding stresses to provide a better fit to body. Another example is EP 0547497B1 (Van Gompel et al.) published on Mar. 26, 1997. This publication discloses a disposable training pant which has stretch gradient side panels to provide an improved fitness. Those conventional pull-on garments try to provide an improved fitness to the body of wearer by controlling forces applied to the waist and leg areas of wearer. However, the improvement in fitness may cause a red marking problem at those areas.

Japanese Laid-Open Patent Publication H8-38546 published on Feb. 13, 1996 discloses a pant type disposable diaper which has a slit formed by not connecting leg portion elastics at the leg opening, to prevent marking of the skin by the leg portion elastics. However, this pull-on garment has a unextensible backsheet in the side panels, which tends to prevent the pull-on garment from providing an improved fitness.

Thus, none of the existing art provides all of the advantages and benefits of the present invention.

SUMMARY

The present invention is directed to a disposable pull-on garment having a longitudinal center line, a front region, a back region and a crotch region between the front region and the back region. The disposable pull-on garment includes a chassis provided in the front, back and crotch regions. The chassis has edge lines in the front and back regions and includes a liquid pervious topsheet, a liquid impervious backsheet associated with the topsheet, and an absorbent core disposed between the topsheet and the backsheet. The disposable pull-on garment further includes at least one pair of extensible ear panels extending laterally outward from the chassis in the front or back region. Each of the ear panels has an outermost edge line. Each of the ear panels are joined to the chassis along the corresponding edge lines to form a seam, thereby forming two leg openings and a waist opening. At least one of the ear panel has, along the seam, a substantially bonded portion starting from the waist opening and an unbonded portion starting from the leg opening. The ratio in length of the unbonded portion to the substantially bonded portion is between about 4:96 and about 20:80.

The present invention is also directed to a method for making such a disposable pull-on garment having a front region, a back region and a crotch region between the front region and the back region. The method includes the steps of preparing the above described chassis, and joining each of the ear panels to the chassis along the corresponding edge lines to form a seam, thereby forming two leg openings and a waist opening.

These and other features, aspects, and advantages of the present invention will become evident to those skilled in the art from reading of the present disclosure.

BRIEF DESCRIPTION OF THE DRAWINGS

While the specification concludes with claims particularly pointing out and distinctly claiming the invention, it is believed that the invention will be better understood from the following description of preferred embodiments which is taken in conjunction with the accompanying drawings and which like designations are used to designate substantially identical elements, and in which:

DETAILED DESCRIPTION

All cited references are incorporated herein by reference in their entireties. Citation of any reference is not an admission regarding any determination as to its availability as prior art to the claimed invention.

Herein, "pull-on garment" refers to articles of wear which have a defined waist opening and a pair of leg openings and which are pulled onto the body of the wearer by inserting the legs into the leg openings and pulling the article up over the waist. Herein, "disposable" describes garments which are not intended to be laundered or otherwise restored or reused as a garment (i.e., they are intended to be discarded after a single use and, preferably, to be recycled, composted or otherwise disposed of in an environmentally compatible manner). A "unitary" pull-on garment refers to pull-on garments which are formed of separate parts united together to form a coordinated entity, but the ear panels are not separate elements joined to a separate chassis; rather, the ear panels are formed by at least one layer which also forms the chassis of the garment (i.e., the garment does not require separately manipulative panels such as a separate chassis and separate ear panels). The pull-on garment is also preferably "absorbent" to absorb and contain the various exudates discharged from the body. A preferred embodiment of the pull-on garment of the present invention is the unitary disposable absorbent pull-on garment, pull-on garment 120, shown in FIG. 1. Herein, "pull-on diaper" refers to pull-on garments generally worn by infants and other incontinent individuals to absorb and contain urine and feces. It should be understood, however, that the present invention is also applicable to other pull-on garments such as training pants, incontinent briefs, feminine hygiene garments or panties, and the like. Herein, "panel" denotes an area or element of the pull-on garment. (While a panel is typically a distinct area or element, a panel may coincide (functionally correspond) somewhat with an adjacent panel.) Herein, "joined" or "joining" encompasses configurations whereby an element is directly secured to another by affixing the element directly to the other element, and configurations whereby the element is indirectly secured to the other element by affixing the element to intermediate member(s) which in turn are affixed to the other element. Herein, "uncontracted state" is used herein to describe states of pull-on garments in its unseamed (i.e., seams are removed), flat and relaxed condition wherein all elastic materials used are removed therefrom.

Figure 1:
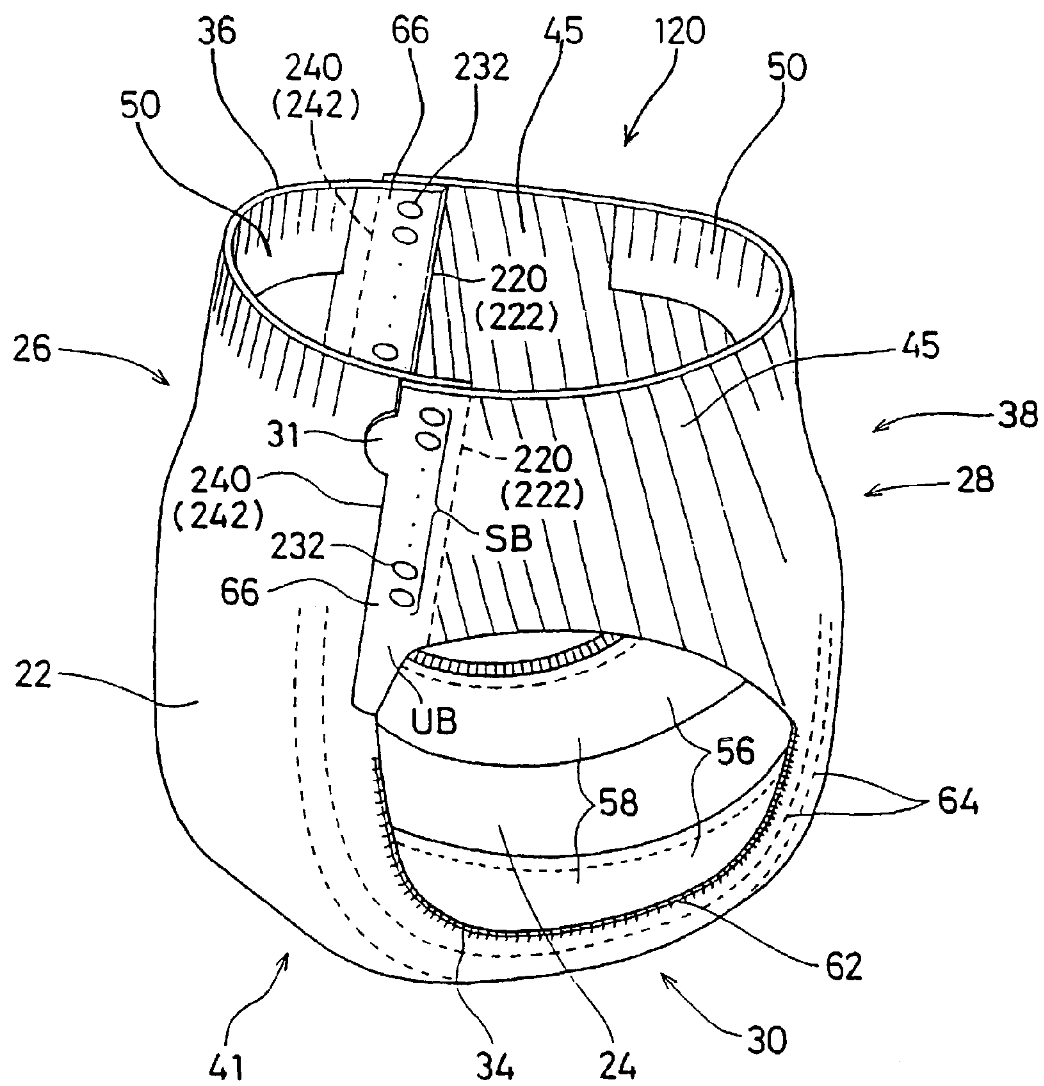
FIG. 1 is a perspective view of one preferred embodiment of the disposable pull-on garment of the present invention in a typical in use configuration.

FIG. 1 shows one preferred embodiment of a disposable pull-on garment of the present invention (i.e., a unitary disposable pull-on diaper 120). Referring to FIG. 1, the disposable pull-on garment 120 of the present invention has a front region 26; a back region 28 and a crotch region 30 between the front region 26 and the back region 28. A chassis 41 is provided in the front, back and crotch regions 26, 28 and 30. The chassis 41 includes a liquid pervious topsheet 24, a liquid impervious backsheet 22 associated with the topsheet 24, and an absorbent core 25 (not shown in FIG. 1) disposed between the topsheet 24 and the backsheet 22. The chassis 41 has side edges 220 which form edge lines 222 in the front region 26.

The pull-on garment 120 of the invention further includes at least one pair of extensible ear panels 45 each extending laterally outward from the corresponding sides of the chassis 41. Each of the ear panels 45 has an outermost edge 240 which forms an outermost edge line 242. At least one of the outermost edge lines 242 has a nonuniform lateral distance from the longitudinal center line 100 (not shown in FIG. 1) in the uncontracted state of the garment 120.

In a preferred embodiment, the ear panels 45 continuously extend from the corresponding sides of the chassis 41 in the back region 28 to the corresponding side edges 220 of the chassis 41 in the front region 26 as shown in FIG. 1. Alternatively, the ear panels 45 may continuously extend from the corresponding sides of the chassis 41 in the front region 26 to the corresponding side edges of the chassis 41 in the back region 28 (not shown in FIG. 1).

The pull-on garment 120 of the invention has the ear panels 45 joined to the chassis 41 to form two leg openings 34 and a waist opening 36. Preferably, the pull-on garment 120 further includes seams 232 each joining the chassis 41 and the ear panels 45 along the corresponding edge lines 222 and 242 to form the two leg openings 34 and the waist opening 36.

In a preferred embodiment, at least one of the ear panels 45 having, along the seam 232, a substantially bonded portion SB starting from the waist opening 36 and an unbonded portion UB starting from the leg opening 34. Preferably, the ratio in length of the unbonded portion to the substantially bonded portion is between about 4:96 and 20:80.

Figure 2:
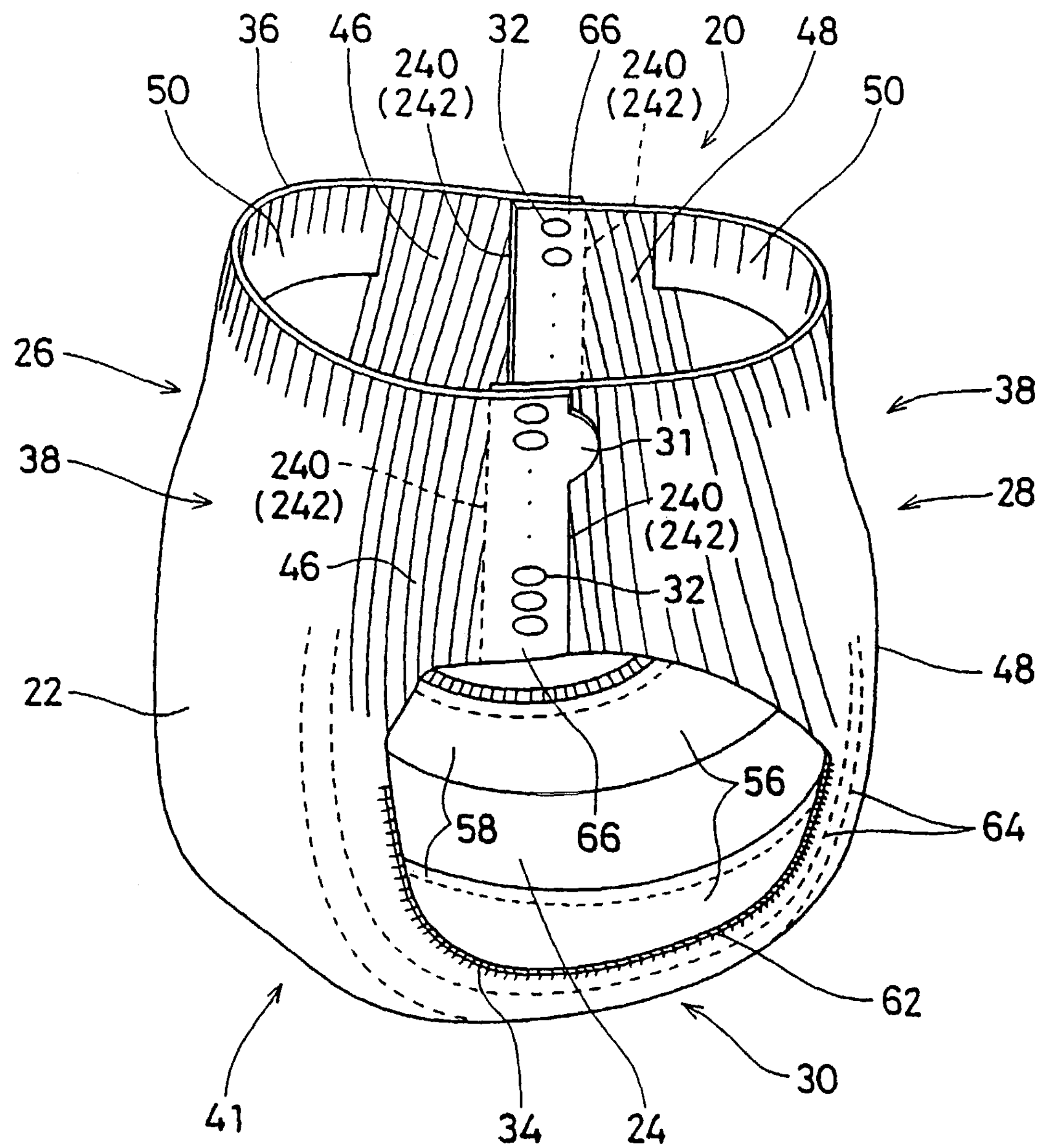
FIG. 2 is a perspective view of another preferred embodiment of the disposable pull-on garment of the present invention in a typical in use configuration.

FIG. 2 shows another preferred embodiment of a disposable pull-on garment of the present invention (i.e., a unitary disposable pull-on diaper 20). Referring to FIG. 2, the disposable pull-on garment 20 includes a pair of extensible front ear panels 46 each extending laterally outward from the corresponding sides of the chassis 41 in the front region 26, and a pair of extensible back ear panels 48 each extending laterally outward from the corresponding sides of the chassis 41 in the back region 28. Each of the ear panels 46 and 48 has an outermost edge 240 which forms an outermost edge line 242. At least one of the outermost edge lines 242 has a nonuniform lateral distance from the longitudinal center line 100 (not shown in FIG. 2 but in FIG. 3) in the uncontracted state of the garment 20. The pull-on garment 20 further includes seams 32 each joining the front and back ear panels 46 and 48 along the corresponding edge lines 242 to form the two leg openings 34 and the waist opening 36.

In a preferred embodiment, at least one of, more preferably both of, the pairs of the ear panels 45, 46 and 48 are elastically extensible in at least the lateral direction. In alternative embodiments, the ear panels 45, 46 and 48 are elastically extensible both in the lateral and longitudinal directions. Herein, "extensible" refers to materials that are capable of extending in at least one direction to a certain degree without undue rupture. Herein, "elasticity" and "elastically extensible" refer to extensible materials that have the ability to return to approximately their original dimensions after the force that extended the material is removed. Herein, any material or element described as "extensible" may also be elastically extensible unless otherwise provided. The extensible ear panels 45, 46 and 48 provide a more comfortable and contouring fit by initially conformably fitting the pull-on garment to the wearer and sustaining this fit throughout the time of wear well past when the pull-on garment has been loaded with exudates since the ear panels 45, 46 and/or 48 allow the sides of the pull-on garment to expand and contract.

The ear panels 45, 46 and 48 may be formed by unitary elements of the pull-on garment 20 or 120 (i.e., they are not separately manipulative elements secured to the pull-on garment 20 or 120, but rather are formed from and are extensions of one or more of the various layers of the pull-on garment).

Figure 3:
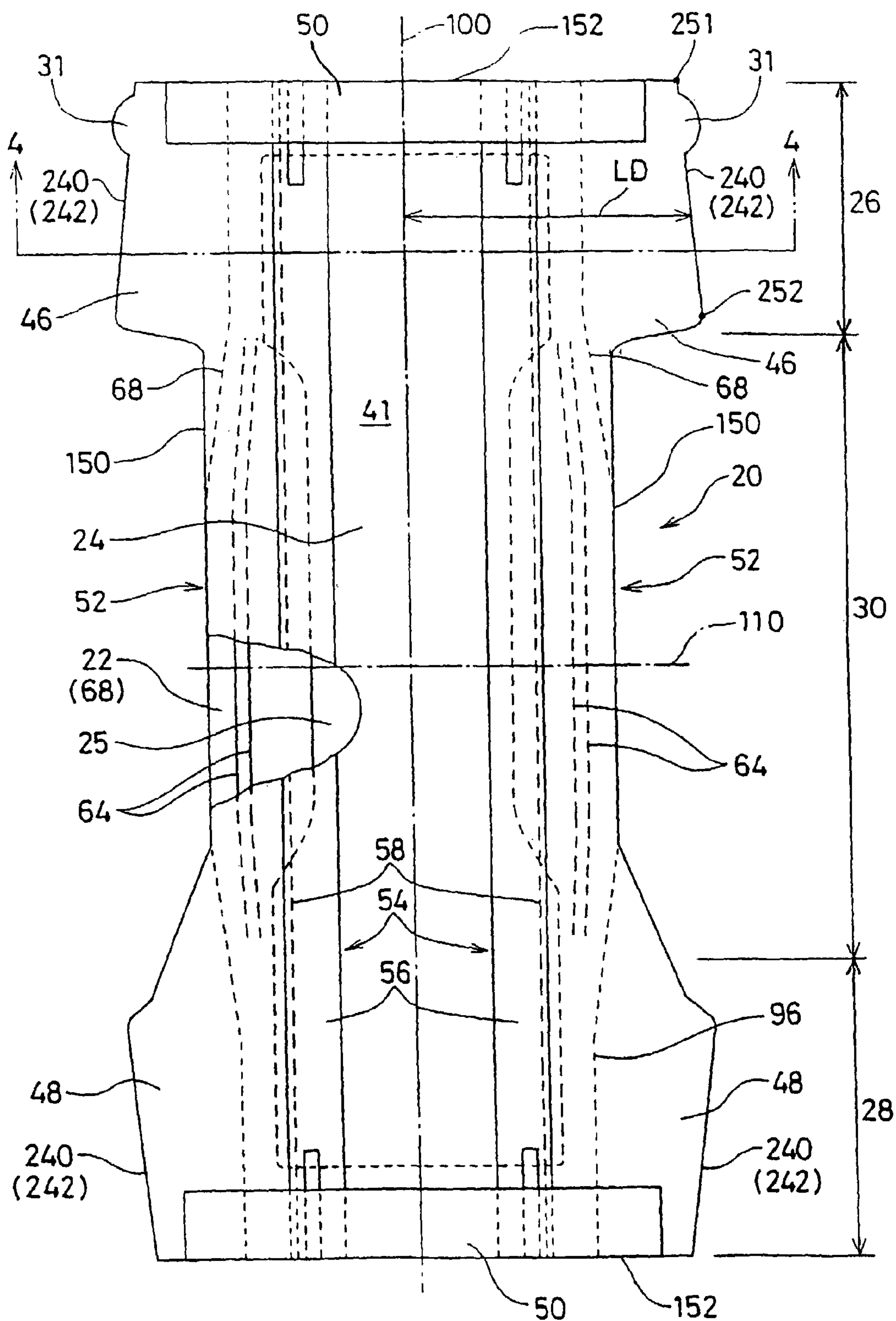
FIG. 3 is a simplified plan view of the embodiment shown in FIG. 2 in its flat uncontracted condition showing the various panels or zones of the garment.

In a preferred embodiment, each of the ear panels 45, 46 and 48 is a projected member of the chassis 41 (more clearly shown in FIG. 3). Preferably, the ear panels 45, 46 and 48 include at least one unitary element or a continuous sheet material (e.g. the nonwoven outer cover 74 in FIG. 4) that forms a part of the chassis 41 and continuously extends into the ear panels 45, 46 and 48. Alternatively, the ear panels 45, 46 and 48 may be discrete members (not shown in FIGS.) which do not have any unitary element that forms a part of the chassis 41, and may be formed by joining the discrete members to the corresponding sides of the chassis 41.

In a preferred embodiment, the pull-on garment 20 or 120 further includes seam panels 66 each extending laterally outward from each of the ear panels 45, 46 and 48; and tear open tabs 31 each extending laterally outward from the seam panel 66. In a preferred embodiment, each of the seam panels 66 is an extension of the corresponding ear panels 45, 46 and 48, or at least one of the component elements used therein, or any other combination of the elements. More preferably, each of the tear open tabs 31 is also an extension of the corresponding seam panel 66 or at least one of its component elements used therein, or any other combination of its elements.

Figure 10:
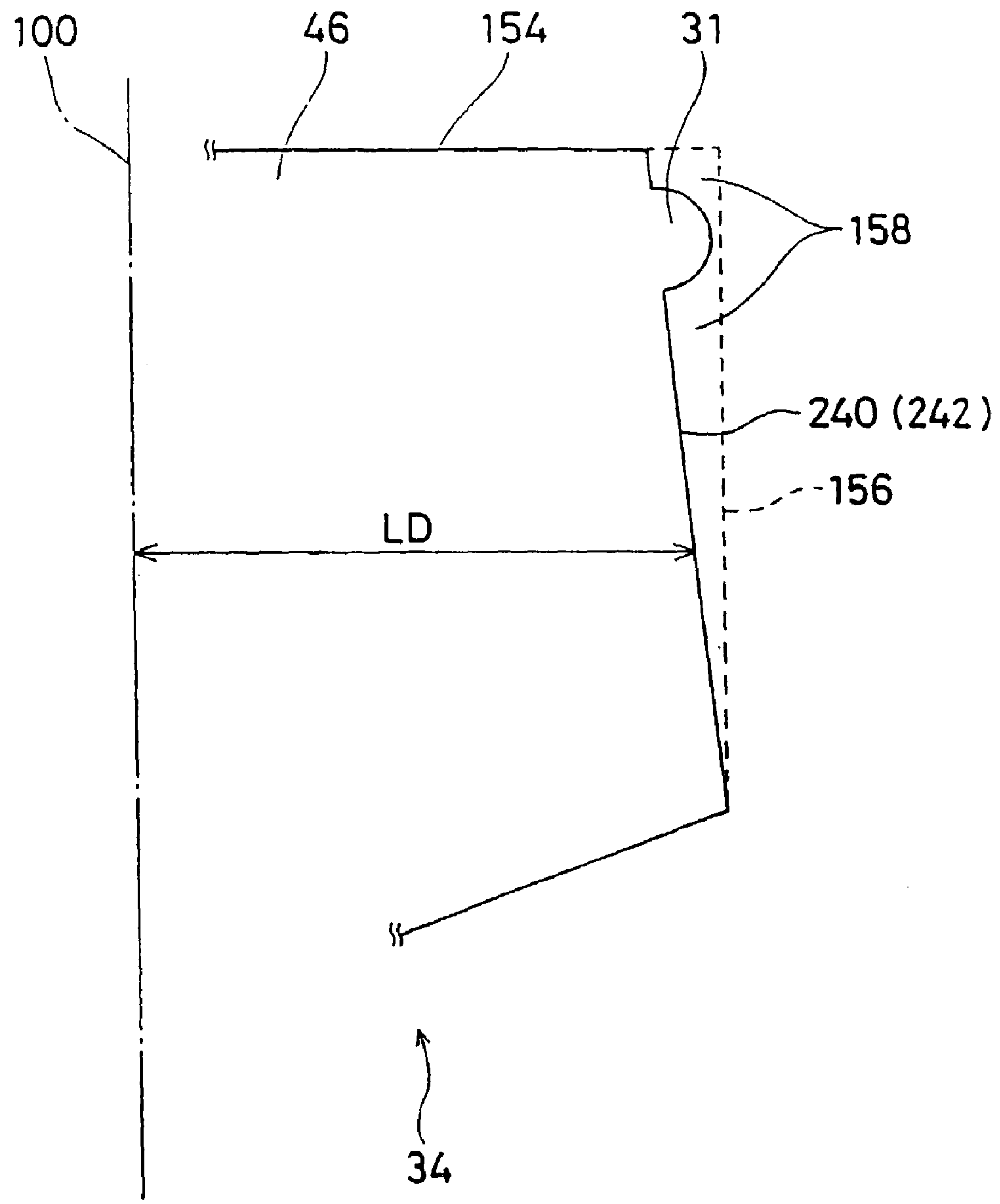
FIG. 10 is a plan view of one embodiment of the front ear panel 46.

The tear open tab 31 can take any shape as long as it facilitates intentional tearing open at the seams 32 after soiling of the pull-on garments 20 and 120. In a preferred embodiment, the lateral distance LD from the longitudinal center line 100 increases towards the leg opening 34 as shown in FIG. 10. In this embodiment, the original material to be used for the front ear panel has a shape defined by the upper material line 154 and the side material line 156 which is perpendicular to the upper material line 154. The outer most edge 240 and the tear open tab 31 are formed by removing (or cutting out) the edge portions 158 from the original material. Since the tear open tab 31 can be obtained within the original material which has the right angle defined by the lines 154 and 156, an effective material use can be achieved (i.e., the original ear panel material can be used effectively).

In a preferred embodiment, the corresponding edge portions of the chassis 41 and/or the ear panels 45, 46 and 48 are seamed directly or indirectly (e.g., through the seam panels 66), in an overlaping manner to make an overlapped seam structure. Alternatively, the front and ear panels 46 and 48 can be seamed in a butt seam manner (not shown in FIGS.). The bonding of the seams 32 can be performed by any suitable means known in the art appropriate for the specific materials employed in the chassis 41 and/or the ear panels 45, 46 and 48. Thus, sonic sealing, heat sealing, pressure bonding, adhesive or cohesive bonding, sewing, autogeneous bonding, and the like may be appropriate techniques. Preferably, the seam panels 66 are joined by a predetermined pattern of heat/pressure or ultrasonic welds which withstands the forces and stresses generated on the garment 20 or 120 during wear.

A continuous belt 38 is formed by the ear panels 45, 46 and 48, and a part of the chassis 41 about the waist opening 36 as shown in FIGS. 1 and 2. Preferably, elasticized waist bands 50 are provided in both the front region 26 and the back region 28. The continuous belt 38 acts to dynamically create fitment forces in the pull-on garment 20 or 120 when positioned on the wearer, to maintain the pull-on garment 20 or 120 on the wearer even when loaded with body exudates thus keeping the absorbent core 25 (not shown in FIG. 2) in close proximity to the wearer, and to distribute the forces dynamically generated during wear about the waist thereby providing supplemental support for the absorbent core 25 without binding or bunching the absorbent core 25.

FIG. 3 is a partially cut-away plan view of the pull-on garment 20 of FIG. 2 in its uncontracted state (except in the ear panels 46 and 48 which are left in their relaxed condition) with the topsheet 24 facing the viewer, prior to the ear panels 46 and 48 being joined together by the seams 32. The pull-on garment 20 has the front region 26, the back region 28 opposed to the front region 26, the crotch region 30 positioned between the front region 26 and the back region 28, and a periphery which is defined by the outer perimeter or edges of the pull-on garment 20 in which the side edges are designated 150 and 240, and the end edges or waist edges are designated 152. The topsheet 24 has the body-facing surface of the pull-on garment 20 which is positioned adjacent to the wearer's body during use. The backsheet 22 has the outer-facing surface of the pull-on garment 20 which is positioned away from the wearer's body. The pull-on garment 20 includes the chassis 41 including the liquid pervious topsheet 24, the liquid impervious backsheet 22 associated with the topsheet 24, and the absorbent core 25 positioned between the topsheet 24 and the backsheet 22. The garment 20 further includes the front and back ear panels 46 and 48 extending laterally outward from the chassis 41, the elasticized leg cuffs 52, and the elasticized waistbands 50. The topsheet 24 and the backsheet 22 have length and width dimensions generally larger than those of the absorbent core 25. The topsheet 24 and the backsheet 22 extend beyond the edges of the absorbent core 25 to thereby form the side edges 150 and the waist edges 152 of the garment 20. The liquid impervious backsheet 22 preferably includes a liquid impervious plastic film 68.

The pull-on garment 20 also has two centerlines, a longitudinal centerline 100 and a transverse centerline 110. Herein, "longitudinal" refers to a line, axis, or direction in the plane of the pull-on garment 20 that is generally aligned with (e.g. approximately parallel with) a vertical plane which bisects a standing wearer into left and right halves when the pull-on garment 20 is worn. Herein, "transverse" and "lateral" are interchangeable and refer to a line, axis or direction which lies within the plane of the pull-on garment that is generally perpendicular to the longitudinal direction (which divides the wearer into front and back body halves). The pull-on garment 20 and component materials thereof also have a body-facing surface which faces the skin of wearer in use and an outer-facing surface which is the opposite surface to the body-facing surface.

Each of the ear panels 45, 46 and 48 of the present invention has the outermost edge line 242. Herein, "edge line" refers to lines which define the outlines of the ear panels 45, 46 and 48 or the chassis 41. Herein, "outermost" refers to portions which are farthest from the longitudinal centerline 100. At least one of the edge lines 242 has a nonuniform lateral distance LD from the longitudinal center line 100 in the uncontracted state of the garment 20.

In a preferred embodiment, the outermost edge line 242 has a first point 251 at the closest portion to the waist opening 36 and a second point 252 at the closest portion to the leg opening 34, and the outermost edge line 242 is a straight line defined by connecting the first and second points 251 and 252. The outermost edge line 242 shows the direction of the outermost edge 240 of the ear panel. In a preferred embodiment, the edge line 242 leans to the longitudinal center line 100 in the uncontracted state of the pull-on garment 20. More preferably, the outermost edge line 242 has, in the uncontracted state of the pull-on garment 20, a lateral distance LD from the longitudinal center line 100 which increases towards the leg opening 34 as shown in FIG. 3. Alternatively, the outermost edge line 242 may have, in the uncontracted state of the pull-on garment 20, a lateral distance LD from the longitudinal center line 100 which decreases towards the leg opening 34 (not shown in FIGS.).

While the topsheet 24, the backsheet 22, and the absorbent core 25 may be assembled in a variety of well known configurations, exemplary chassis configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 entitled "Absorbent Article With Dynamic Elastic Waist Feature Having A Predisposed Resilient Flexural Hinge" which issued to Kenneth B. Buell et al., on Sep. 29, 1992.

Figure 4:
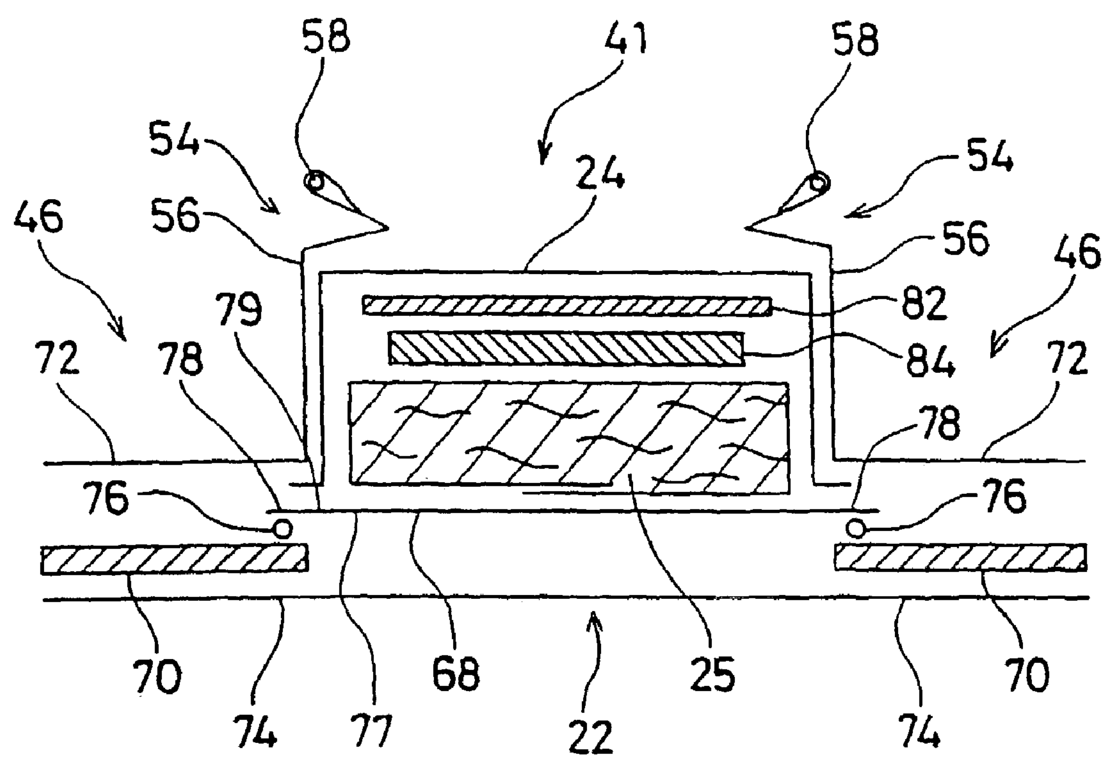
FIG. 4 is a cross-sectional view of a preferred embodiment taken along the section line 4-4 of FIG. 3.

FIG. 4 is a cross-sectional view of a preferred embodiment taken along the section line 4-4 of FIG. 3. The pull-on garment 20 includes the chassis 41 including the liquid pervious topsheet 24, the liquid impervious backsheet 22 associated with the topsheet 24, and the absorbent core 25 positioned between the topsheet 24 and the backsheet 22. The pull-on garment further includes the front ear panels 46 each extending laterally outward from the chassis 41, and an inner barrier cuffs 54. Although FIG. 4 depicts only the structure of the front ear panel 46 and the chassis 41 in the front region 26, preferably a similar structure is also provided in the back region 28. In a preferred embodiment, each of the front ear panels 46 is formed by a lamination of an extended part 72 of the barrier flap 56, an elastic member 70 and the nonwoven outer cover 74. The elastic member 70 includes a plane elastomeric material 124 (not shown in FIG. 4 but in FIG. 6). Herein, "plane elastomeric material" refers to elastomeric materials which continuously extend in two dimensional directions. Preferred plane elastomeric materials include a scrim, a perforated (or apertures formed) film, an elastomeric woven or nonwoven, and the like. In a preferred embodiment, the plane elastomeric material 124 includes at least a portion that has a nonuniform lateral width.

Figure 5:
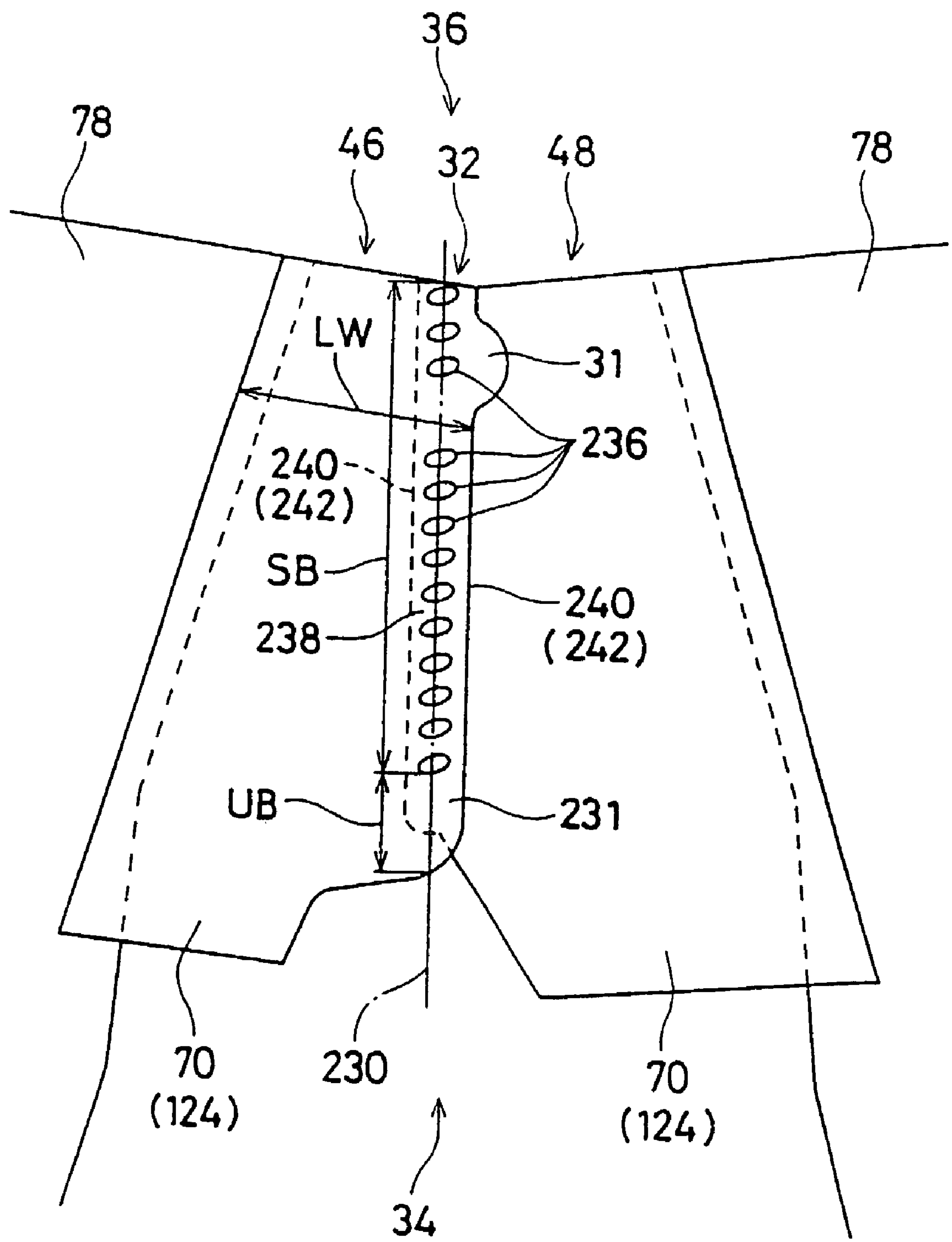
FIG. 5 is a more detailed plan view of the front and back ear panels 46 and 48 which are shown in FIG. 2.

FIG. 5 is a more detailed plan view of the front and back ear panels 46 and 48 shown in FIG. 2. In FIG. 5, the nonwoven outer cover 74 is removed from the ear panels 46 and 48 to clearly show the elastic members 70 and the seam 32. In a preferred embodiment, each of the ear panels 46 and 48 includes the elastic member 70 which includes a plane elastomeric material 124 (such as the one shown in FIG. 6). The elastic member 70 may further include an extensible sheet or film material (e.g., a nonwoven material) which is joined to the plane elastomeric material 124.

In a preferred embodiment, the plane elastomeric material 124 has an identical shape and dimensions with the elastic member 70. The elastic member 70 and the plane elastomeric material 124 may take a wide variety of sizes and shapes (e.g., triangular, rectangular, other quadrilateral, and other polygon). In a preferred embodiment, the plane elastomeric material 124 has at least a portion that has a nonuniform lateral width LW. Preferably, the lateral width LW of the plane elastomeric material 124 increases towards the leg opening 34 as shown in FIG. 5. Alternatively, the lateral width LW of the plane elastomeric material 124 may decrease towards the leg opening 34 (not shown in FIGS.).

In a preferred embodiment, the seam 32 is formed on a seaming line 230 which is preliminary determined along the edge lines 242. The seaming line 230 can be determined from any straight lines which may be drawn in the overlapped area 238 between the edge lines 242. More preferably, the seaming line 230 is formed along, more preferably in parallel with, the corresponding edge lines 242. In a more preferred embodiment, a straight line which equally divides the overlapped area 238 is chosen as the seaming line 230 as shown in FIG. 5.

In a preferred embodiment, the seaming line 230 leans to the longitudinal center line 100 in the uncontracted state of the garment 20. Preferably, the lateral distance of the seaming line 230 from the longitudinal center line 100 increases toward the leg opening 34. Alternatively, the lateral distance of the seaming line 230 from the longitudinal center line 100 decreases toward the leg opening 34 (not shown in FIGS.).

A preferred seam 32 is formed by a plurality of discrete spaced apart seaming bonds 236 which are formed on the seaming line 230 as shown in FIG. 5. The discrete seaming bonds 236 form, on the seaming line 230, a substantially bonded portion SB starting from the waist opening 36 and an unbonded portion UB starting from the leg opening 34. Herein, "substantially bonded portion" refers to portions which are intermittently and/or continuously joined to other materials to contribute to the formation of the leg and waist openings 34 and 36. Herein, "unbonded portion" refers to portions which are not joined to other materials.

In an alternative embodiment, the seam 32 may be formed by a continuous bond which continuously bonds the front and back ear panels 46 and 48 on the seaming line 230 (not shown in FIGS.). The continuous bond also forms, on the seaming line 230, a substantially bonded portion SB starting from the waist opening 36 and an unbonded portion UB starting from the leg opening 34.

To avoid a red marking problem on wearer's skin, the preferred ratio in length of the unbonded portion UB to the substantially bonded portion SB is from about 4:96 to about 20:80, more preferably from about 8:92 to about 15:85, yet more preferably from about 10:90 to about 13:87. Preferred disposable pull-on garments for infants have an unbonded portion UB from the leg opening 34, in length, from about 4 mm to about 20 mm, more preferably from about 8 mm to about 15 mm, yet more preferably from about 10 mm to about 13 mm.

In a preferred embodiment, at least one of the ear panels 45, 46 and 48 is partially shaped to form a tear open tab 231 associated with the unbonded portion UB for an easy tear open after soiling. The tear open tab 231 can take any shape as long as it facilitates intentional tearing open at the seams 32. In this embodiment, the ear panels 45, 46 and 48 can be torn open from the leg opening 34 after soiling. Thus, the original tear open tab 31 can be eliminated in this embodiment.

The method for making a disposable pull-on garment 20 or 120 of the present invention includes the step of preparing the chassis 41 provided in the front, back and crotch regions 26, 28, and 30 and having edge lines 222 in the front and back regions 26 and 28. The method further includes the step of joining each of the ear panels 45, 46 and 48 to the chassis 41 along the corresponding edge lines 222 and 242 to form a seam 32 and 232, thereby forming two leg openings 34 and a waist opening 36, so that at least one of the ear panels 45, 46 and 48 has, along the seam 32, the substantially bonded portion SB starting from the waist opening 36 and the unbonded portion UB starting from the leg opening 34. The ratio in length of the unbonded portion UB to the substantially bonded portion SB is between about 4:96 and about 20:80.

The absorbent core 25 can be any absorbent member which is generally compressible, conformable, non-irritating to the wearer's skin, and capable of absorbing and retaining liquids such as urine and other certain body exudates. The absorbent core 25 may be manufactured in a wide variety of sizes and shapes (e.g., rectangular, hourglass, "T"-shaped, asymmetric, etc.) and from a wide variety of liquid-absorbent materials commonly used in disposable pull-on garments and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

In a preferred embodiment of the invention, the absorbent core 25 has, in the uncontracted state of the pull-on garment 20, an area ratio of the core area to the garment area of greater than about 25%, more preferably greater than about 40%. The core area is defined as the total area of the body-facing surface of the absorbent core 25 in the uncontracted state of the pull-on garment 20. The periphery of the body-facing surface of the absorbent core 25 is determined by the outline of aggregates of primary absorbent materials used in the absorbent core 25. Herein, "primary absorbent material" refers to absorbent materials which occupy more than about 80% in dry state volume of the absorbent core 25. In a preferred embodiment, a wood pulp (e.g., airfelt) is considered a primary absorbent material of the absorbent core 25 and defines the periphery of the body-facing surface of the absorbent core 25, thus defining the core area of the absorbent core 25. The other primary absorbent materials may include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The garment area is defined as the total area of the body-facing surface of the pull-on garment 20 in the uncontracted state. Therefore, the area ratio is calculated as follows:

$$AR=CA/GA\times 100$$

wherein,

AR: the area ratio (%)

CA: the core area ($cm^2$)

GA: the total area ($cm^2$)

In a preferred embodiment for infant use, the absorbent core 25 has a core area of less than about 450 $cm^2$, more preferably less than about 425 $cm^2$. Preferably, the absorbent core 25 has a maximum core width of less than about 12 cm, more preferably less than about 11 cm. Herein, "core width" refers to the lateral distance from one side edge to the other side edge of the absorbent core 25.

The configuration and construction of the absorbent core 25 may vary (e.g., the absorbent core 25 may have varying caliper zones, a hydrophilic gradient, a superabsorbent gradient, or lower average density and lower average basis weight acquisition zones; or may include one or more layers or structures). Further, the size and absorbent capacity of the absorbent core 25 may also be varied to accommodate wearers ranging from infants through adults. However, the total absorbent capacity of the absorbent core 25 should be compatible with the design loading and the intended use of the garment 20.

A preferred embodiment of the garment 20 has an asymmetric, modified hourglass-shaped absorbent core 25 having ears in the front and back waist regions 26 and 28. Other exemplary absorbent structures for use as the absorbent core 25 that have achieved wide acceptance and commercial success are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989.

The chassis 41 may further include an acquisition/distribution core 84 of chemically stiffened fibers positioned over the absorbent core 25, thereby forming a dual core system. In a preferred embodiment, the fibers are hydrophilic chemically stiffened cellulosic fibers. Herein, "chemically stiffened fibers" means any fibers which have been stiffened by chemical means to increase stiffness of the fibers under both dry and aqueous conditions. Such means include the addition of chemical stiffening agents which, for example, coat and/or impregnate the fibers. Such means also include the stiffening of the fibers by altering the chemical structure of the fibers themselves, e.g., by cross-linking polymer chains.

The fibers utilized in the acquisition/distribution core 84 can also be stiffened by means of chemical reaction. For example, crosslinking agents can be applied to the fibers which, subsequent to application, are caused to chemically form intrafiber crosslink bonds. These crosslink bonds can increase stiffness of the fibers. Whereas the utilization of intrafiber crosslink bonds to chemically stiffen the fibers is preferred, it is not meant to exclude other types of reactions for chemical stiffening of the fibers.

In the more preferred stiffened fibers, chemical processing includes intrafiber crosslinking with crosslinking agents while such fibers are in a relatively dehydrated, defibrated (i.e. individualized), twisted, curled condition. Suitable chemical stiffening agents include monomeric crosslinking agents including, but not limited to, $C_2$-$C_8$ dialdehydes and $C_2$-$C_8$ monoaldehydes having an acid functionality can be employed to form the crosslinking solution. These compounds are capable of reacting with at least two hydroxyl groups in a single cellulose chain or on proximately located cellulose chains in a single fiber. Such crosslinking agents contemplated for use in preparing the stiffened cellulose fibers include, but are not limited to, glutaraldehyde, glyoxal, formaldehyde, and glyoxylic acid. Other suitable stiffening agents are polycarboxylates, such as citric acid. The polycarboxylic stiffening agents and a process for making stiffened fibers from them are described in U.S. Pat. No. 5,190,563, entitled "Process for Preparing Individualized, Polycarboxylic Acid crosslinked Fibers" issued to Herron, on Mar. 2, 1993. The effect of crosslinking under these conditions is to form fibers which are stiffened and which tend to retain their twisted, curled configuration during use in the absorbent articles herein. Such fibers, and processes for making them are cited in the above incorporated patents.

Preferred dual core systems are disclosed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992. In a preferred embodiment, the acquisition/distribution core 84 includes chemically treated stiffened cellulosic fiber material, available from Weyerhaeuser Co. (U.S.A.) under the trade designation of "CMC". Preferably, the acquisition/distribution core 84 has a basis weight of from about 40 $g/m^2$ to about 400 $g/m^2$, more preferably from about 75 $g/m^2$ to about 300 $g/m^2$.

More preferably, the chassis 22 further includes an acquisition/distribution layer 82 between the topsheet 24 and the acquisition/distribution core 84 as shown in FIG. 4. The acquisition/distribution layer 82 is provided to help reduce the tendency for surface wetness of the topsheet 24. The acquisition/distribution layer 82 preferably includes carded, resin bonded hiloft nonwoven materials such as, for example, available as Code No. FT-6860 from Polymer Group, Inc., North America (Landisiville, N.J., U.S.A.), which is made of polyethylene telephthalate fibers of 6 dtex, and has a basis weight of about 43 g/m$^2$. A preferable example for the acquisition/distribution layer 82 and the acquisition/distribution core 84 is disclosed in EP 0797968A1 (Kurt et al.) published on Oct. 1, 1997.

The topsheet 24 is preferably compliant, soft feeling, and non-irritating to the wearer's skin. Further, the topsheet 24 is liquid pervious permitting liquids (e.g., urine) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be included of natural fibers (e.g., wood or cotton fibers), synthetic fibers (e.g., polymeric fibers such as polyester, polypropylene, or polyethylene fibers) or from a combination of natural and synthetic fibers. The topsheet 24 is preferably made of a hydrophobic material to isolate the wearer's skin from liquids which have passed through the topsheet 24 and are contained in the absorbent core 25 (i.e., to prevent rewet). If the topsheet 24 is made of a hydrophobic material, at least the upper surface of the topsheet 24 is treated to be hydrophilic so that liquids will transfer through the topsheet more rapidly. This diminishes the likelihood that body exudates will flow off the topsheet 24 rather than being drawn through the topsheet 24 and being absorbed by the absorbent core 25. The topsheet 24 can be rendered hydrophilic by treating it with a surfactant. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991.

In a preferred embodiment, the topsheet 24 is a nonwoven web that can provide reduced tendency for surface wetness; and consequently facilitate maintaining urine absorbed by the core 25 away from the user's skin, after wetting. One of the preferred topsheet materials is a thermobonded carded web which is available as Code No. P-8 from Fiberweb North America, Inc. (Simpsonville, S.C., U.S.A.). Another preferred topsheet material is available as Code No. S-2355 from Havix Co., Japan. This material is a bi-layer composite material, and made of two kinds of synthetic surfactant treated bicomponent fibers by using carding and air-through technologies. Yet another preferred topsheet material is a thermobonded carded web which is available as Code No. Profleece Style 040018007 from Amoco Fabrics, Inc. (Gronau, Germany).

In a preferred embodiment, the topsheet 24 is compatible with other materials (e.g., component materials in the backsheet 22) used in the pull-on garment 20 or 120, in terms of its design/process, for forming ventilation holes along the waist edge 152 and/or at other portions of the pull-on garment 20 or 120.

Another preferred topsheet 24 includes an apertured formed film. Apertured formed films are preferred for the topsheet 24 because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", issued to Thompson on Dec. 30, 1975; U.S. Pat. No. 4,324,246 entitled "Disposable Absorbent Article Having A Stain Resistant Topsheet", issued to Mullane, et al. on Apr. 13, 1982; U.S. Pat. No. 4,342,314 entitled "Resilient Plastic Web Exhibiting Fiber-Like Properties", issued to Radel. et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", issued to Ahr et al. on Jul. 31, 1984; and U.S. Pat. No. 5,006,394 "Multilayer Polymeric Film" issued to Baird on Apr. 9, 1991.

In a preferred embodiment, the backsheet 22 includes the liquid impervious film 68 as shown in, for example, FIG. 4. Preferably, the liquid impervious film 68 longitudinally extends in the front, back and crotch regions 26, 28 and 30. More preferably, the liquid impervious film 68 does not laterally extend into the at least one of the ear panels 46 or 48. The liquid impervious film 68 has a body-facing surface 79 and an outer-facing surface 77. The liquid impervious film 68 is impervious to liquids (e.g., urine) and is preferably manufactured from a thin plastic film. However, more preferably the plastic film permits vapors to escape from the garment 20. In a preferred embodiment, a microporous polyethylene film is used for the liquid impervious film 68. A suitable microporous polyethylene film is manufactured by Mitsui Toatsu Chemicals, Inc., Nagoya, Japan and marketed in the trade as PG-P. In a preferred embodiment, a disposable tape (not shown in FIGS.) is additionally joined to the outer surface of the backsheet 22 to provide a convenient disposal after soiling.

A suitable material for the liquid impervious film 68 is a thermoplastic film having a thickness of from about 0.012 mm (0.5 mil) to about 0.051 mm (2.0 mils), preferably including polyethylene or polypropylene. Preferably, the liquid impervious film has a basis weight of from about 5 g/m$^2$ to about 35 g/m$^2$. However, it should be noted that other flexible liquid impervious materials may be used. Herein, "flexible" refers to materials which are compliant and which will readily conform to the general shape and contours of the wearer's body.

Preferably, the backsheet 22 further includes the nonwoven outer cover 74 which is joined with the outer-facing surface of the liquid impervious film 68 to form a laminate (i.e., the backsheet 22). The nonwoven outer cover 74 is positioned at the outermost portion of the garment 20 and covers at least a portion of the outermost portion of the garment 20. In a preferred embodiment, the nonwoven outer cover 74 covers almost all of the area of the outermost portion of the garment 20. The nonwoven outer cover 74 may be joined to the liquid impervious film 68 by any suitable attachment means known in the art. For example, the nonwoven outer cover 74 may be secured to the liquid impervious film 68 by a uniform continuous layer of adhesive, a patterned layer of adhesive, or an array of separate lines, spirals, or spots of adhesive. Suitable adhesives include a hotmelt adhesive obtainable from Nitta Findley Co., Ltd., Osaka, Japan as H-2128, and a hotmelt adhesive obtainable from H.B. Fuller Japan Co., Ltd., Osaka, Japan as JM-6064.

In a preferred embodiment, the nonwoven outer cover 74 is a carded nonwoven web, for example, obtainable from Havix Co., LTD., Gifu, Japan as E-2341. The nonwoven outer cover 74 is made of bi-component fibers of a polyethylene (PE) and a polypropylene (PP). The ratio of PE/PP is about 50/50. The PE/PP bi-component fiber has the dimension of 2d×51 mm. Another preferred carded nonwoven web is obtainable from Chisso Corp., Moriyama, Japan. The nonwoven outer cover 74 is also made of bi-component fibers of a polyethylene (PE) and a polypropylene (PP). The ratio of PE/PP is about 50/50.

In another preferred embodiment, the nonwoven web is a spunbonded nonwoven web, for example, obtainable from Mitsui Petrochemical Industries, Ltd., Tokyo, Japan. The nonwoven web is made of bi-component fibers of a polyethylene (PE) and a polypropylene (PP). The ratio of PE/PP is about 80/20. The PE/PP bi-component fiber has the thickness is approximately 2.3d.

In a preferred embodiment, the backsheet 22 is compatible with other materials (e.g., component materials in the topsheet 24) used in the pull-on garment 20 or 120, in terms of its design/process, for forming ventilation holes along the waist edge 152 and/or for forming seams 32 in the pull-on garment 20 or 120.

The backsheet 22 is preferably positioned adjacent the outer-facing surface of the absorbent core 25 and is preferably joined thereto by any suitable attachment means known in the art. For example, the backsheet 22 may be secured to the absorbent core 25 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn., U.S.A., and marketed as HL-1358J. An example of a suitable attachment means including an open pattern network of filaments of adhesive is disclosed in U.S. Pat. No. 4,573,986 entitled "Disposable Waste-Containment Garment", which issued to Minetola et al. on Mar. 4, 1986. Another suitable attachment means including several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment means may include heat bonds, pressure bonds, ultrasonic bonds, dynamic mechanical bonds, or any other suitable attachment means or combinations of these attachment means as are known in the art.

In an alternative embodiment, the absorbent core 25 is not joined to the backsheet 22, and/or the topsheet 24 in order to provide greater extensibility in the front region 26 and the back region 28.

The pull-on garment 20 preferably further includes elasticized leg cuffs 52 for providing improved containment of liquids and other body exudates. The elasticized leg cuffs 52 may include several different embodiments for reducing the leakage of body exudates in the leg regions. (The leg cuffs can be and are sometimes also referred to as leg bands, side flaps, barrier cuffs, elastic cuffs or gasketing cuffs.) U.S. Pat. No. 3,860,003 entitled "Contractable Side Portions for Disposable Diaper" issued to Buell on Jan. 14, 1975, describes a disposable diaper which provides a contractible leg opening having a side flap and one or more elastic members to provide an elasticized leg cuff. U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987; and U.S. Pat. No. 4,795,454 entitled "Absorbent Article Having Leakage-Resistant Dual Cuffs" issued to Dragoo on Jan. 3, 1989, describe disposable diapers having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinence garment having side-edge-leakage-guard gutters configured to contain free liquids within the garment.

While each elasticized leg cuff 52 may be configured so as to be similar to any of the leg bands, side flaps, barrier cuffs, or elastic cuffs described above, it is preferred that the elasticized leg cuff 52 includes an elastic gasketing cuff 62 with one or more elastic strands 64 as shown in FIG. 3, which is described in the above-referred U.S. Pat. Nos. 4,695,278 and 4,795,454. It is also preferred that each elasticized leg cuff 52 further includes inner barrier cuffs 54 each including a barrier flap 56 and a spacing means 58 which are described in the above-referenced U.S. Pat. No. 4,909,803.

The pull-on garment 20 preferably further includes an elasticized waistband 50 that provides improved fit and containment. The elasticized waistband 50 is that portion or zone of the pull-on garment 20 which is intended to elastically expand and contract to dynamically fit the wearer's waist. The elasticized waistband 50 preferably extends longitudinally outwardly from the waist edge of the pull-on garment 20 toward the waist edge of the absorbent core 25. Preferably, the pull-on garment 20 has two elasticized waistbands 50, one positioned in the back region 28 and one positioned in the front region 26, although other pull-on diaper embodiments can be constructed with a single elasticized waistband. The elasticized waistband 50 may be constructed in a number of different configurations including those described in U.S. Pat. No. 4,515,595 entitled "Disposable Diapers with Elastically Contractible Waistbands" issued to Kievit et al. on May 7, 1985 and the above referenced U.S. Pat. No. 5,151,092 issued to Buell.

The waistbands 50 may include materials that have been "prestrained" or "mechanically prestrained" (i.e., subjected to some degree of localized pattern mechanical stretching to permanently elongate the material). The materials may be prestrained using deep embossing techniques as are known in the art. Alternatively, the materials may be prestrained by directing the material through an incremental mechanical stretching system as described in U.S. Pat. No. 5,330,458 entitled "Absorbent Article With Elastic Feature Having A Portion Mechanically Prestrained" issued to Buell et al., on Jul. 19, 1994. The materials are then allowed to return to their substantially untensioned condition, thus forming a zero strain stretch material that is extensible, at least up to the point of initial stretching. Examples of zero strain materials are disclosed in U.S. Pat. No. 2,075,189 issued to Galligan on Mar. 30, 1937; U.S. Pat. No. 3,025,199 issued to Harwood on Mar. 13, 1962; U.S. Pat. Nos. 4,107,364 and 4,209,563 issued to Sisson on Aug. 15, 1978 and Jun. 24, 1980, respectively; U.S. Pat. No. 4,834,741 issued to Sabee on May 30, 1989; and U.S. Pat. No. 5,151,092 issued to Buell et al., on Sep. 29, 1992.

At least one of the ear panels 45, 46 and 48 includes the elastic member 70 as shown in FIG. 4. The elastic member 70 of the front ear panels 46 includes the elastomeric material 124 (not shown in FIG. 4) which preferably extends laterally outward from the chassis 41 to provide good fitness by generating the optimal retention (or sustained) force at the waist and side areas of the wearer. Preferably, the elastomeric material 124 is extensible in at least one direction, preferably in the lateral direction to generate a retention (or sustained) force that is optimal to prevent the pull-on garment 20 from drooping, sagging, or sliding down from its position on the torso without causing the red marking on the skin of the wearer. In a preferred embodiment, each of the ear panels 45, 46 and 48 includes the elastomeric material 124.

The elastic member 70 is operatively joined to at least one of the nonwoven webs 72 and 74 in the ear panels 45, 46 and 48 to allow the elastic member 70 to be elastically extensible in at least the lateral direction. In a preferred embodiment, the elastic member 70 is operatively joined to the nonwoven webs 72 and 74 by securing them to at least one, preferably both of the nonwoven webs 72 and 74 while in a substantially untensioned (zero strain) condition.

The elastic member 70 can be operatively joined to the nonwoven webs 72 and 74, by using either an intermittent bonding configuration or a substantially continuous bonding configuration. Herein, "intermittently" bonded laminate web means a laminate web wherein the plies are initially bonded to one another at discrete spaced apart points or a laminate web wherein the plies are substantially unbonded to one another at discrete spaced apart areas. Conversely, a "substantially continuously" bonded laminate web means a laminate web wherein the plies are initially bonded substantially continuously to one another throughout the areas of interface. It is preferred that the stretch laminate be bonded over all or a significant portion of the stretch laminate so that the inelastic webs (i.e., the nonwoven webs 72 and 74) elongate or draw without causing rupture, and the layers of the stretch laminates are preferably bonded in a configuration that maintains all of the layers of the stretch laminate in relatively close adherence to one another after the incremental mechanical stretching operation. Consequently, the elastic panel members and the other plies of the stretch laminate are preferably substantially continuously bonded together using an adhesive. In a particularly preferred embodiment, the adhesive selected is applied with a control coat spray pattern at a basis weight of about 7.0 grams/square m. The adhesive pattern width is about 6.0 cm. The adhesive is preferably an adhesive such as is available from Nitta Findley Co., Ltd., Osaka, Japan, under the designation H2085F. Alternatively, the elastic panel member and any other components of the stretch laminates may be intermittently or continuously bonded to one another using heat bonding, pressure bonding, ultrasonic bonding, dynamic mechanical bonding, or any other method as is known in the art.

After the elastic member 70 is operatively joined to at least one of the nonwoven webs 72 and 74, at least a portion of the resultant composite stretch laminate is then subjected to mechanical stretching sufficient to permanently elongate the non-elastic components which are, for example, the nonwoven webs 72 and 74. The composite stretch laminate is then allowed to return to its substantially untensioned condition. At least one pair of, preferably both of the ear panels 45, 46 and 48 is thus formed into "zero strain" stretch laminates. (Alternatively, the elastic member 70 could be operatively joined in a tensioned condition and then subjected to mechanical stretching; although this is not as preferred as a "zero strain" stretch laminate.) Herein, "zero strain" stretch laminate refers to a laminate included of at least two plies of material which are secured to one another along at least a portion of their coextensive surfaces while in a substantially untensioned ("zero strain") condition; one of the plies including a material which is stretchable and elastomeric (i.e., will return substantially to its untensioned dimensions after an applied tensile force has been released) and a second ply which is elongatable (but not necessarily elastomeric) so that upon stretching the second ply will be, at least to a degree, permanently elongated so that upon release of the applied tensile forces, it will not fully return to its original undeformed configuration. The resulting stretch laminate is thereby rendered elastically extensible, at least up to the point of initial stretching, in the direction of initial stretching. Particularly preferred methods and apparatus used for making stretch laminates utilize meshing corrugated rolls to mechanically stretch the components. Particularly preferred apparatus and methods are disclosed in U.S. Pat. No. 5,167,897 issued to Weber et al. on Dec. 1, 1992; U.S. Pat. No. 5,156,793 issued to Buell et al. on Oct. 20, 1990; and U.S. Pat. No. 5,143,679 issued to Weber et al. on Sep. 1, 1992.

The elastic member 70 is preferably joined to, more preferably directly secured to the respective edges 78 of the liquid impervious film (i.e., the liquid impervious film 68) through an adhesive 76 as shown in FIG. 4. In a preferred embodiment, while liquid impervious film 68 longitudinally extends in the front, back and crotch regions 26, 28 and 30, it does not laterally extend into at least one of, preferably each of the extensible ear panels 45, 46 and 48. In a more preferred embodiment, the elastic member 70 is joined to the respective edges 78 of the liquid impervious film 68 at the outer-facing surface 77 as shown in FIG. 4. In an alternative embodiment, the elastic member 70 may be joined to the respective edges 78 of the liquid impervious film 68 at the body-facing surface 79 (not shown in FIGS.). Preferably, the adhesive 76 is applied in a spiral glue pattern. In a preferred embodiment, the adhesive 76 is a flexible adhesive with an amorphous and crystallizing component. Such a preferred adhesive is made by Nitta Findley Co., Ltd., Osaka, Japan, under the designation H2085F. Alternatively, the elastic member 70 may be joined to the respective edges 78 of the liquid impervious film 68 by any other bonding means known in the art which include heat bonds, pressure bonds, ultrasonic bonds, dynamic mechanical bonds, or combinations of these attachment means.

Figure 6:
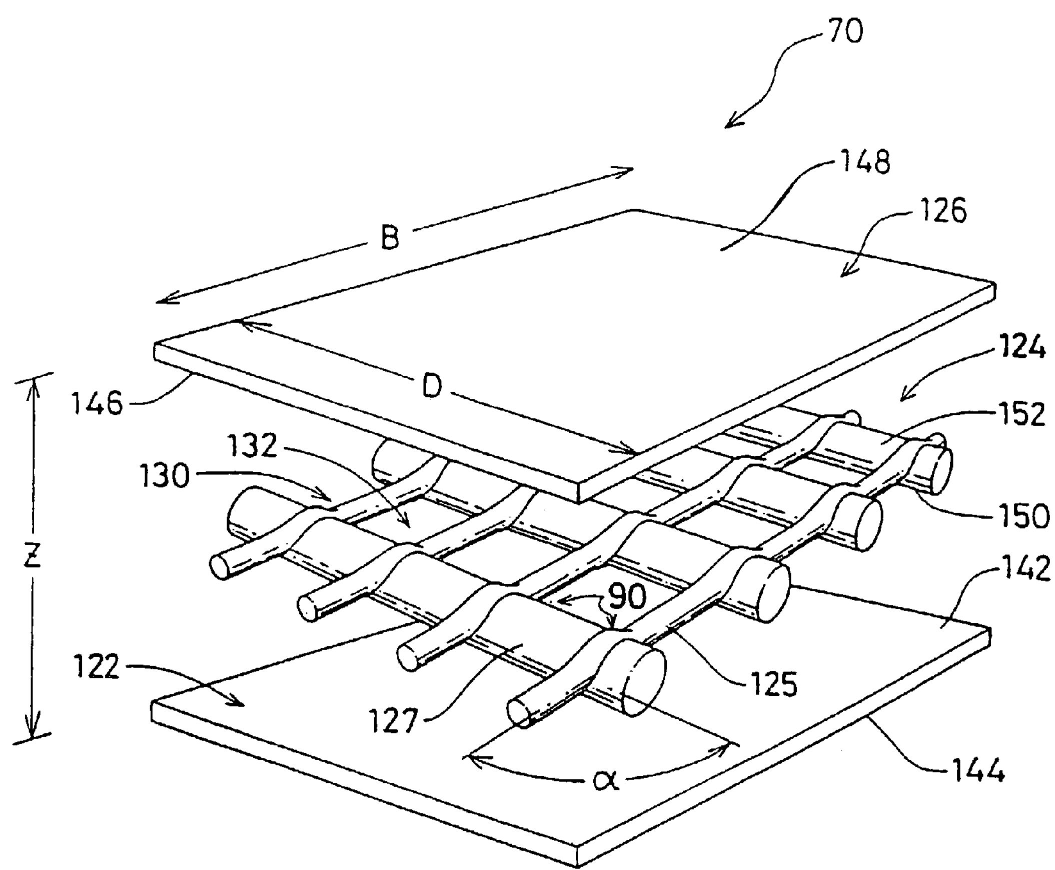
FIG. 6 is a cross-sectional view of an elastic member 70 of a preferred embodiment.

Referring to FIG. 6, the elastic member 70 includes the elastomeric material 124 having a first surface 150 and a second surface 152 opposing the first surface 150, and a first coverstock layer 122 which is joined to the first surface 150 of the elastomeric material 124. In a preferred embodiment, the first coverstock layer 122 is joined to the first surface 150 of the elastomeric material 124 by an adhesive 160 as shown, for example, in FIG. 7. More preferably, the elastic member 70 further includes a second coverstock layer 126 which is joined to the second surface 152 of the elastomeric material 124 by an adhesive 164.

Preferably, the elastic member 70 is joined to the respective edges 78 of the liquid impervious film 68 at the outer-facing surface 77 as shown in FIG. 4. In an alternative embodiment, the elastic member 70 may be joined to the respective edges 78 of the liquid impervious film 68 at the body-facing surface 79 (not shown in FIGS.).

The elastomeric material 124 may be formed in a wide variety of sizes, forms and shapes. In a preferred embodiment, the elastomeric material 124 is in the form of a continuous plane layer. Preferred forms of continuous plane layer include a scrim, a perforated (or apertures formed) film, an elastomeric woven or nonwoven, and the like. The continuous plane layer may take any shape which can be suitably provided in the ear panels. Preferred shapes of continuous plane layer include a quadrilateral including a rectangle and a square, a trapezoid, and the other polygons. In an alternative embodiment, the elastomeric material 124 is in the form of discrete strands (or strings) which are not connected each other.

Elastomeric materials which have been found to be especially suitable for the elastomeric material 124 are styrenic block copolymer based scrim materials, perforated (or apertured) elastic films, preferably with a thickness of from about 0.05 mm to about 1.0 mm (0.002 inch-0.039 inch). Other suitable elastomeric materials for the elastomeric material 124 include "live" synthetic or natural rubber, other synthetic or natural rubber foams, elastomeric films (including heat shrinkable elastomeric films), elastomeric woven or non-woven webs, elastomeric composites, or the like.

Figure 9:
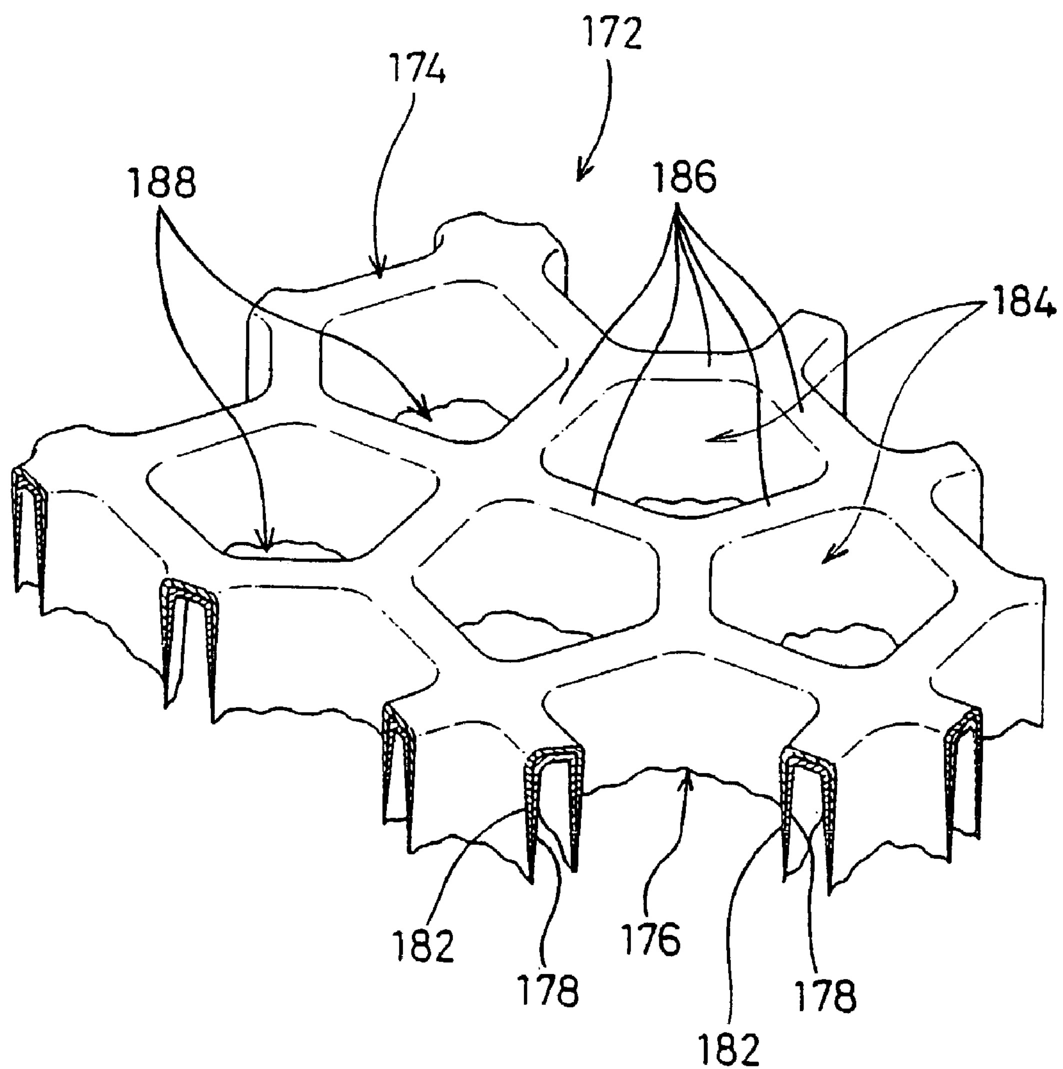
FIG. 9 is a fragmentary enlarged perspective illustration of an alternative embodiment of the elastomeric material.

In a preferred embodiment, the elastomeric material 124 is a porous, macroscopically-expanded, three-dimensional elastomeric web 172 as shown in FIG. 9. The web 172 has a continuous first surface 174 and a discontinuous second surface 176 remote from first surface 174. The elastomeric web 172 preferably comprises a formed film having at least two polymeric layers, with at least one of the layers being an elastomer layer 178 and at least one of the other layers being a substantially less elastomeric skin layer 182. The elastomeric web exhibits a multiplicity of primary apertures 184 in the first surface 174 of the web 172, the primary apertures 184 being defined in the plane of the first surface 174 by a continuous network of interconnecting members 186. Each interconnecting member 186 exhibits an upwardly concave-shaped cross-section along its length. The interconnecting members 186 terminate substantially concurrently with one another to form a secondary aperture 188 in the plane of the second surface of the web. The primary apertures 184 may have any shape. The detail of such a structure and the method to manufacture is disclosed in U.S. patent application Ser. No. 08/816,106, filed Mar. 14, 1997. A preferred porous elastomeric material 124 is manufactured by the Tredegar Film Products under the designation X-25007.

The extension properties of the side elastomeric material 124 such as the First Cycle Extension Force at 100% Extension (FCEF100%), the First Cycle Extension Force at 200% Extension (FCEF200%), the Second Cycle Recovery Force at 50% Extension (SCRF50%) and sustained load at 50% after 10-12 hours are important considerations in the performance of disposable garments. The side elastomeric material 124 preferably has extension properties within the defined ranges herein. The FCEF100% and the FCEF200% are measures of the overall perceived "stretchiness" during application/removal of disposable garments. These two properties also effect the ability of the applicator to achieve a suitable degree of application stretch. A side elastomeric material 124 with a relatively high FCEF100% and FCEF200% can cause difficulty in applying the disposable garment onto the wearer. On the other hand, a side elastomeric material 124 with a relatively low FCEF100% and FCEF200% may not achieve a suitable level of body fitting/conformity. The SCRF50% also closely relates to the body fitting/conformity of disposable garments for the wearer. A side elastomeric material 124 with a relatively high SCRF50% tends to cause red marking on the skin of the wearer and may be uncomfortable for the wearer during usage. A side elastomeric material 124 with a relatively low SCRF50% may not provide enough elastic force to keep the diaper in place on the wearer or may not provide good body fit. The sustained load at 50% after 10-12 hours evaluates the force decay over time. This force decay should be limited or substantial sagging will result.

The values of FCEF100%, FCEF200% and SCRF50% can be measured by using a tensile tester. The tensile tester includes an upper jaw and a lower jaw which is located below the upper jaw. The upper jaw is movable and is connected to an extension force measuring means. The lower jaw is fixed at a desk (or floor). A test specimen (i.e., the elastomeric material to be measured) which has about 2.54 cm (1.0 inch) in width and about 12.75 cm (5 inches) in length is prepared and clamped between the upper jaw and the lower jaw so that the effective specimen length (L) (i.e., gauge length) is about 5.08 cm (2.0 inches). The extension force is applied to the test specimen through the upper jaw. When no extension force is applied to the test specimen, the test specimen is in its original length (i.e., 0% extension). A tensile tester suitable for use herein is available from Instron Corporation (100 Royall Street, Canton, Mass. 02021, U.S.A.) as Code No. Instron 5564.

Figure 8:
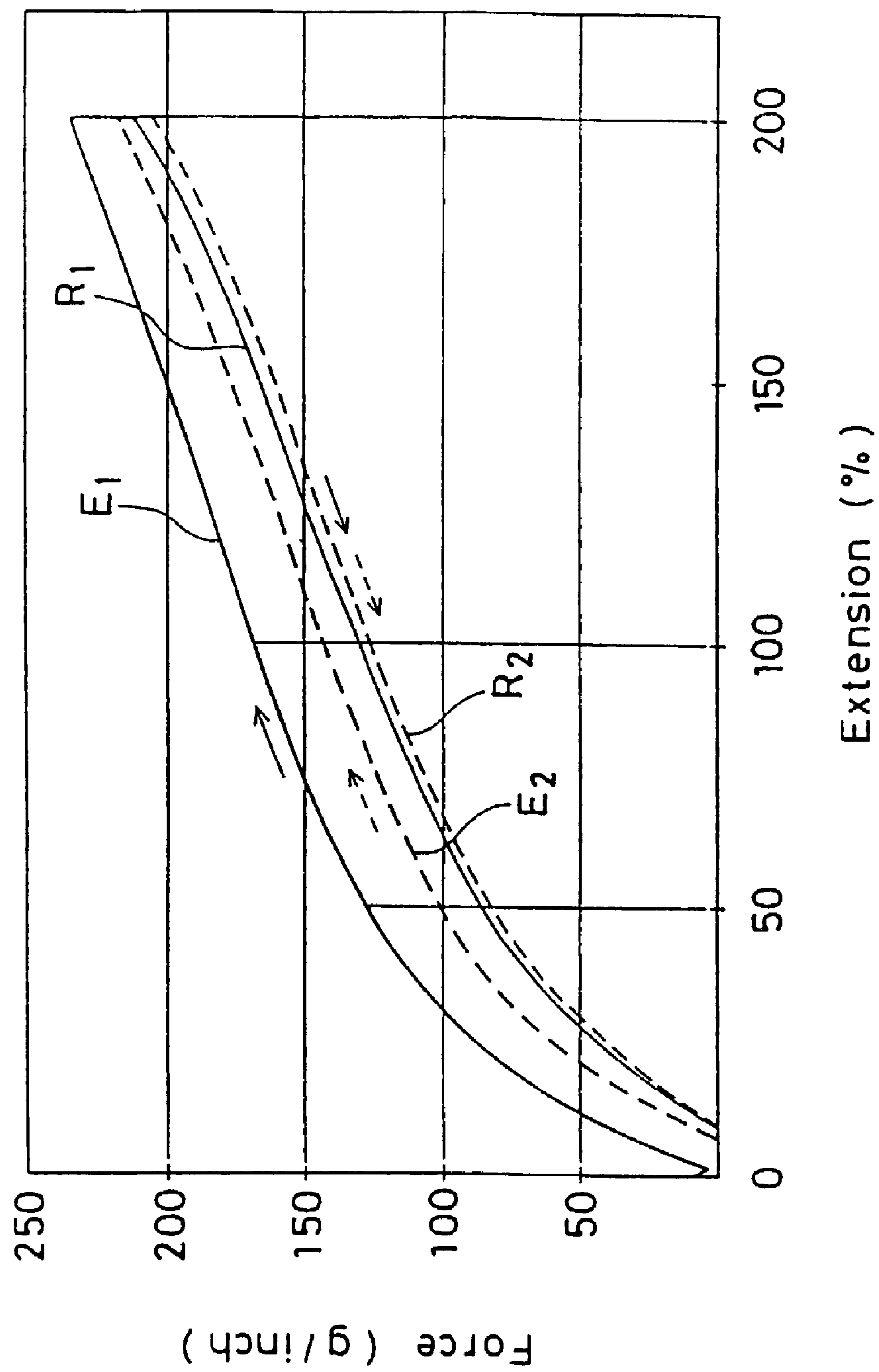
FIG. 8 is a graph showing the two-cycles of hysteresis curves of an elastomeric material, in a preferred embodiment.

FIG. 8 shows one preferred example of the extension and recovery force curves for the two cycle hysteresis of the elastomeric material 124. The curve E1 shows the extension force in the first cycle, while the curve R1 shows the recovery force in the first cycle. The curve E2 (shown in dashed lines) shows the extension force in the second cycle, while the curve R2 shows the recovery force in the second cycle. The extension and recovery properties are measured as follows.

In the first cycle, the test specimen is subjected to an initial extension force at a crosshead rate of 50.8 cm/min (20 in/min) at about 23° C. and held for 30 seconds at 200% extension. The test specimen is then allowed to relax at the same rate to the original state (i.e., 0% extension). The test specimen is allowed to remain unconstrained for one minute before being subjected to a second extension force (for the second cycle) at the same rate and conditions.

In preferred embodiments, the FCEF100% of the side elastomeric material 124 is at least about 100 grams/inch. More preferably, the FCEF100% is between about 120 to about 220 grams/inch, most preferably between about 150 grams/inch and 190 grams/inch. The FCEF200% is preferably between about 160 grams/inch and about 450 grams/inch, more preferably between about 180 grams/inch and about 300 grams/inch, and yet more preferably between about 200 grams/inch and about 240 grams/inch. The SCRF50% of the side elastomeric material 124 is preferably between about 40 grams/inch and about 130 grams/inch, more preferably between about 65 grams/inch and about 105 grams/inch, and yet more preferably between about 75 grams/inch and about 95 grams/inch. The sustained load at 50% after 10-12 hours is preferably between about 40 grams/inch and about 130 grams/inch, more preferably between about 65 grams/inch and about 105 grams/inch, and yet more preferably between about 75 grams/inch and about 95 grams/inch.

In the preferred embodiment shown in FIG. 6, the elastomeric scrim 124 has a plurality of first strands 125 and a plurality of second strands 127. The plurality of first strands 125 intersect the plurality of second strands 127 at nodes 130 at a predetermined angle α, forming a net-like open structure having a plurality of apertures 132. Each aperture 132 is defined by at least two adjacent first strands and at least two adjacent second strands, so that the apertures 132 are substantially rectangular in shape. Other configurations of the apertures 132, such as parallelograms, squares, or circular arc segments, can also be provided. Preferably, the first and second strands 125 and 127 are substantially straight and substantially parallel to one another. Preferably, the first strands 125 intersect the second strands 127 at nodes 130 such that the angle α is about 90 degrees. The first and second strands 125 and 127 are preferably joined or bonded at nodes 90.

A preferred elastomeric scrim 124 is manufactured by the Conwed Plastics Company (Minneapolis, Minn., U.S.A.) under the designation XO2514. This material has about 12 elastic strands per inch in the structural direction B (i.e., the first strands 125) and about 7 elastic strands per inch in the structural direction D (i.e., the second strands 127).

In the embodiment shown in FIG. 6, the elastic member 70 includes first and second coverstock layers 122 and 126, and elastomeric material 124 disposed in the first and second coverstock layers 122 and 126. The first coverstock layer 122 has an inner surface 142 and an outer surface 144. The inner surface 142 of the first coverstock layer 122 is the surface that is positioned facing the elastomeric material 124. The second coverstock layer 126 also has an inner surface 146 and an outer surface 148. The inner surface 146 of the second coverstock layer 126 is the surface that is positioned facing the elastomeric material 124. The elastomeric material 124 also has two planar surfaces, first surface 150 and second surface 152, each of which is substantially parallel with the planes of the first and second coverstock layers 122 and 126. The first surface 150 is that planar surface of the elastomeric material 124 that is most closely adjacent with the inner surface 142 of first coverstock layer 122. The second surface 152 is that planar surface of elastomeric material 124 that is most closely adjacent to the inner surface 146 of the second coverstock layer 126.

Since the elastic member 70 will be subjected to mechanical stretching before and during use, the first and second coverstock layers 122 and 126 preferably have a relatively high elongation at breaking, and are more preferably stretchable or elongatable, yet more preferably drawable (but not necessarily elastomeric), without undue (and preferably without any), tearing or ripping. Further, the first and second coverstock layers 122 and 126 are preferably compliant, soft feeling, and non-irritating to the wearer's skin and give the article the feel and comfort of a cloth garment. Suitable materials for the first and second coverstock layers 122 and 126 can be manufactured from a wide range of materials such as plastic films, apertured plastic films, woven or nonwoven webs of natural fibers (e.g., wood or cotton fibers), synthetic fibers (e.g., polyolefins, polyamides, polyester, polyethylene, or polypropylene fibers), or a combination of natural and/or synthetic fibers, or coated woven or nonwoven webs.

Preferably, each of the first and second coverstock layers 122 and 126 is an identical consolidated nonwoven material. An exemplary preferred nonwoven material is manufactured by the Fiberweb North America, Inc. (Simpsonville, S.C., U.S.A.) under the designation Sofspan 200. This material has a basis weight of 25 $g/m^2$ before consolidation and a basis weight of about 63 g/m2 after consolidation. Herein, "basis weight" is the weight of one square meter of planar web material. Alternatively, highly strainable nonwoven materials may be used. Alternatively, the first and second coverstock layers 122 and 126 need not be of identical materials, as long as the desired performance requirements, such as elastic performance, softness, flexibility, breathability and durability, are met. Herein, "consolidated nonwoven material" means a nonwoven material that has been gathered or necked under mechanical tension in the structural direction D so that the material can elongate in the structural direction D under low force.

Figure 7:
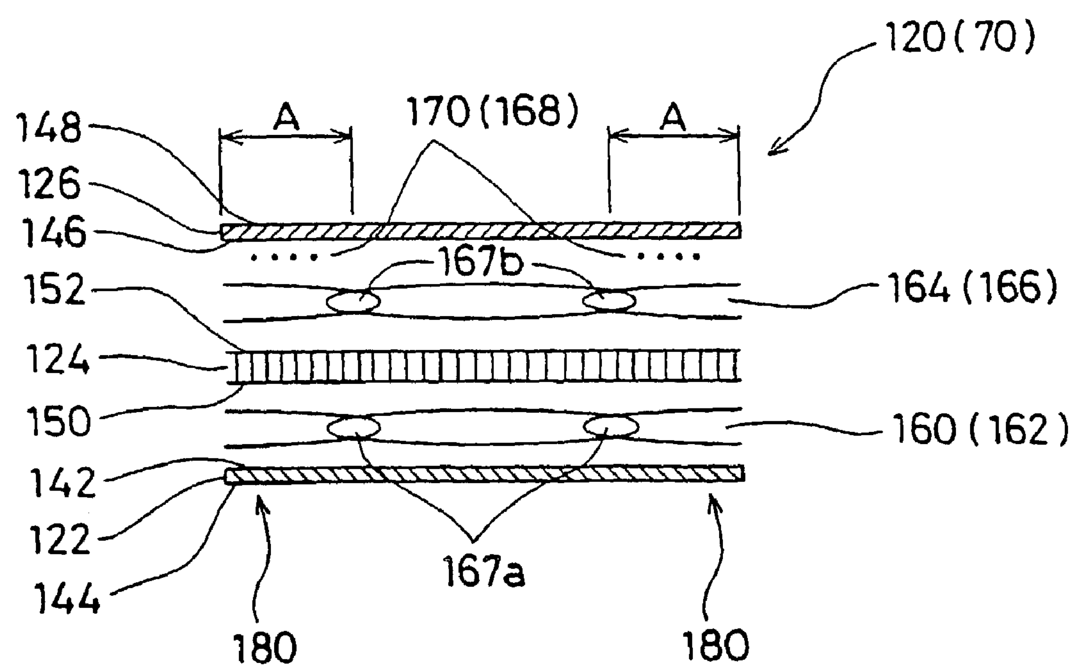
FIG. 7 is a fragmentary enlarged side view of the elastic member 70 shown in FIG. 4.

FIG. 7 shows a fragmentary enlarged side view looking into the structural direction B of the laminate 120 (i.e., the elastic member 70). It has been found that when the laminate 120 is bonded or otherwise anchored such that side anchor zones A are created, such a laminate 120 is both highly elastic and substantially free from delamination and creep, while providing very good performance characteristics in all performance categories with no trade-offs between any performance characteristics required. The side anchoring is preferably performed by side gluing with adhesive beads to anchor the elastomeric material 124 between the coverstock layers 122 and 126 as a part of the lamination process. Alternatively, side anchoring may be performed by sewing, heat sealing, ultrasound bonding, needle punching, alternative gluing processes, or by any other means known to those skilled in the art. Another alternative is to side anchor the layers of the laminate structure after the lamination of the elastomeric and coverstock components has been performed.

Preferably, the laminate 120 may particularly provide very good soft feel for the wearer and for the consumer. This is important because consumers value softness. In conventional laminates, the attempts to eliminate creep have frequently required an unacceptable decrease in softness, often accompanied by an unacceptable decrease in an ability to activate. This is because such previous attempts (which have fallen short of eliminating creep) have focused on the application of additional melt blown adhesive, often in an overall coating pattern, in the attempt to strengthen the bonds. This has generally resulted in an undesirable overall stiffening of the laminate. However, the laminates of the preferred embodiments provide elimination of creep without the loss of consumer-desired soft feel and without compromise of activation ability.

Referring to FIG. 7, a first adhesive 170 is applied to the inner surface 146 of the second coverstock layer 126 in positions that correspond to each of the outer edges 180 of the laminate structure 120. The first adhesive 170 may alternatively or additionally be applied to the inner surface 142 of the first coverstock layer 122. For ease of illustration, the description and FIGS. refer to application to the second coverstock layer 126 only.

This pattern creates side anchor zones A, which substantially eliminate the delamination and creep associated with previously known laminates and which allows the laminate 120 to experience higher strains without creeping or delaminating. It has also been found that confining the first adhesive 170 to the edge areas 180 of the laminate structure 120 avoids impeding the extensibility of the laminate 120 and also avoids tears in the coverstock layers 122 and 126. Preferably, the first adhesive 170 is applied as a plurality of beads 168, as shown in FIG. 7. Preferably, the first adhesive 170 is a flexible adhesive with an amorphous and crystallizing component. Such a preferred adhesive is made by Nitta Findley Co., Ltd., Osaka, Japan, under the designation H9224.

More preferably, the laminate 120 includes a second adhesive 164. The second adhesive 164 is preferably applied to the second surface 152 of the elastomeric material 124, but could alternatively be applied to the first surface 150 of the elastomeric material 124. The second adhesive 164 is preferably applied in a spiral spray pattern 166, thereby forming bond points **167*b* that are more discrete than would be formed by a linear spray application. Without being bound by theory, it is believed that most of the second adhesive 164 is sprayed in the structural direction D (FIG. 6**). Thus, it has been found that spiral spraying results in very good activation properties. Herein, "activation" refers to the ability to stretch.

It has been found that spraying the layer of second adhesive 164 directly onto the second surface 152 of the elastomeric material 124 is more preferable than applying the second adhesive 164 to the opposing (i.e., second) coverstock layer 126. This is because the second adhesive 164 tends to penetrate through any residual processing agents or oils that may remain on the surface of the elastomeric material 124. Such residual materials, if left to remain on the elastomeric material 124, may weaken the adhesive bonds and thus the laminate structure 120 over time. For example, if these residual materials are left intact, the bonds used to form the laminate 120 may weaken during the time interval prior to consumer purchase of the product.

Peel values for the laminate 120 in the spiral adhesive areas are typically higher when the spirals 166 are applied directly to the elastomeric material 124 than to the opposing (i.e., second) coverstock layer 126. Herein, "peel value" refers to the amount of force required to separate the two layers of coverstock material, 122 and 126, from each other. Higher peel values typically equate to less chance of delamination in use.

A third adhesive 160 may also preferably be applied to the inner surface 142 of the first coverstock layer 122. Preferably, the third adhesive 160 is an elastomeric adhesive. In a manner similar to that described with reference to the second spiral adhesive application 166, the first adhesive 160 is preferably applied in a spiral spray pattern 162, thereby forming bond points 167*a* that are more discrete than would be formed by a linear spray application. Without being bound by theory, it is believed that most of the first adhesive 160 so sprayed aligns in the structural direction D.

Preferably, second and third adhesives 160 and 164 are the same elastomeric adhesive. A preferred adhesive for use in the second and third adhesive spiral sprays 162 and 166 is made by Nitta Findley Co., Ltd., Osaka, Japan, under the designation H2120. Preferably, the add-on level for each of the second and third spiral sprays 162 and 166 is about 4 to about 12 milligrams per square inch, more preferably about 8 milligrams per square inch.

It is understood that the examples and embodiments described herein are for illustrative purpose only and that various modifications or changes will be suggested to one skilled in the art without departing from the scope of the present invention.

What is claimed is:

1. A disposable pull-on garment having a front region, a back region and a crotch region between the front region and the back region, comprising:

a chassis provided in the front, back and crotch regions and having edge lines in the front and back regions, the chassis including a topsheet, a backsheet associated with the topsheet, and an absorbent core disposed between the topsheet and the backsheet; and a pair of extensible front ear panels extending laterally outward from the chassis in the front region, and a pair of extensible back ear panels extending laterally outward from the chassis in the back region, each of the front and back ear panels having an outermost edge line; each of the front and back ear panels being joined along its outermost edge line to its corresponding opposite front or back ear panel to form two overlapping seams, two leg openings and a waist opening; at least one of the overlapping seams having a substantially bonded portion extending from the waist opening to an unbonded portion and the unbonded portion extending from the substantially bonded portion to one of the leg openings such that the ratio in the length of the unbonded portion to the substantially bonded portion is between about 4:96 and about 20:80;

wherein the unbonded portion has a length of 4-20 millimeters.

2. The disposable pull-on garment of claim 1 wherein at least one of the front and back ear panels is shaped to form a tear open tab associated with the unbonded portion for gripping by the user for easy tear opening.

3. The disposable pull-on garment of claim 1 wherein at least one of the front and back ear panels is formed from a zero strain stretch laminate.

4. The disposable pull-on garment of claim 1, wherein the topsheet is liquid pervious.

5. The disposable pull-on garment of claim 1, wherein the backsheet is liquid impervious.

6. The disposable pull-on garment of claim 1, wherein the ratio is between about 8:92 and about 15:85.

7. The disposable pull-on garment of claim 1, wherein the ratio is between about 10:90 and about 13:87.

8. The disposable pull-on garment of claim 1, wherein the ratio in the length of the unbonded portion to the substantially bonded portion is between 4:96 and 20:80.

9. The disposable pull-on garment of claim 1, wherein the unbonded portion starts at one of the leg openings.

10. The disposable pull-on garment of claim 9, wherein the substantially bonded portion starts at the waist opening.

11. The disposable pull-on garment of claim 1, wherein the unbonded portion has a length of 8-15 millimeters.

12. The disposable pull-on garment of claim 1, wherein the unbonded portion has a length of 8-15 millimeters.

* * * * *